United States Patent
Otsuka et al.

(10) Patent No.: US 11,667,609 B2
(45) Date of Patent: Jun. 6, 2023

(54) COMPOUND, COMPOSITION CONTAINING SAID COMPOUND, SELF-HEALING MATERIAL, SURFACE COATING AGENT, PAINT, ADHESIVE, MATERIAL FOR BATTERY AND CURED PRODUCT

(71) Applicants: ADEKA CORPORATION, Tokyo (JP); TOKYO INSTITUTE OF TECHNOLOGY, Tokyo (JP)

(72) Inventors: Hideyuki Otsuka, Tokyo (JP); Daisuke Aoki, Tokyo (JP); Daisuke Sawamoto, Tokyo (JP); Atsushi Kobayashi, Tokyo (JP); Satoyuki Chikaoka, Tokyo (JP)

(73) Assignees: ADEKA CORPORATION, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 130 days.

(21) Appl. No.: 17/434,139

(22) PCT Filed: Feb. 20, 2020

(86) PCT No.: PCT/JP2020/006838
§ 371 (c)(1),
(2) Date: Aug. 26, 2021

(87) PCT Pub. No.: WO2020/175321
PCT Pub. Date: Sep. 3, 2020

(65) Prior Publication Data
US 2022/0153698 A1   May 19, 2022

(30) Foreign Application Priority Data

Feb. 28, 2019   (JP) .............................. JP2019-036118

(51) Int. Cl.
| | |
|---|---|
| C07D 211/96 | (2006.01) |
| C09D 7/63 | (2018.01) |
| C08K 5/43 | (2006.01) |
| C09J 11/06 | (2006.01) |
| H01M 4/62 | (2006.01) |

(52) U.S. Cl.
CPC .............. C07D 211/96 (2013.01); C08K 5/43 (2013.01); C09D 7/63 (2018.01); C09J 11/06 (2013.01); H01M 4/622 (2013.01)

(58) Field of Classification Search
CPC ................................. C07D 211/96; C08K 5/43
See application file for complete search history.

(56) References Cited

FOREIGN PATENT DOCUMENTS

| | | | |
|---|---|---|---|
| EP | 2 597 110 | * | 11/2011 |
| JP | 2017-202980 | | 11/2017 |
| JP | 2017-218519 | | 12/2017 |
| WO | 2007/069765 | | 6/2007 |

(Continued)

OTHER PUBLICATIONS

International Search Report dated Apr. 7, 2020 in International (PCT) Application No. PCT/JP2020/006838.

(Continued)

Primary Examiner — Doris L Lee
(74) Attorney, Agent, or Firm — Wenderoth, Lind & Ponack, L.L.P.

(57) ABSTRACT

Provided is a compound, which is represented by the following general formula (1):

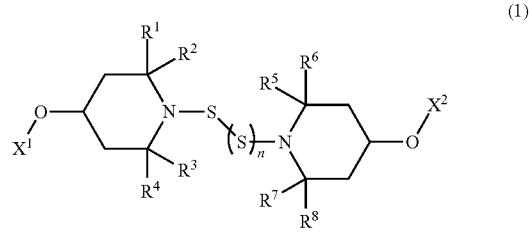

where $X^1$ and $X^2$ each independently represent an acrylic group or a methacrylic group, $R^1$ to $R^8$ each independently (Continued)

Example 2    Comparative Example 1

Example 2    Comparative Example 1 represent a hydrogen atom or a hydrocarbon group having 1 to 6 carbon atoms, and "n" represents an integer of from 1 to 10.

10 Claims, 1 Drawing Sheet

(56) References Cited

FOREIGN PATENT DOCUMENTS

| WO | 2013/162019 | 10/2013 |
|----|-------------|---------|
| WO | 2014/201290 | 12/2014 |
| WO | 2016/006413 | 1/2016  |

OTHER PUBLICATIONS

Takahashi et al., "Thermally Healable and Reprocessable Bis(hindered amino)disulfide-Cross-Linked Polymethacrylate Networks", ACS Macro Letters, 2017, vol. 6, No. 11, pp. 1280-1284.

Tsuruoka et al., "Fusion of Different Crosslinked Polymers Based on Dynamic Disulfide Exchange", Angewandte Chemie, International Edition, Dec. 30, 2019, vol. 59, No. 11, pp. 4294-4298.

Tsurumi et al., "A Strategy toward Cyclic Topologies Based on Dynamic Behavior of a Bis(hindered amino)disulfide Linker", Angewandte Chemie, International Edition, Jan. 9, 2020, vol. 59, No. 11, pp. 4269-4273.

Takahashi, Akira et al., "Thermally Adjustable Dynamic Disulfide Linkages Mediated by Highly Air-Stable 2,2,6,6-Tetramethylpiperidine-1-sulfanyl (TEMPS) Radicals", Angewandte Chemie International Edition, vol. 56, No. 8, 2017, pp. 2016-2021.

Jin, Kailong et al., "Recyclable Crosslinked Polymer Networks via One-Step Controlled Radical Polymerization", Advanced Materials, vol. 28, No. 31, 2016, pp. 6746-6750.

Bin Rusayyis, Mohammed et al., "Recyclable Polymethacrylate Networks Containing Dynamic Dialkylamino Disulfide Linkages and Exhibiting Full Property Recovery", Macromolecules, vol. 53, No. 19, 2020, pp. 8367-8373.

Extended European Search Report dated Jun. 24, 2022 in corresponding European Patent Application No. 20763394.2.

* cited by examiner

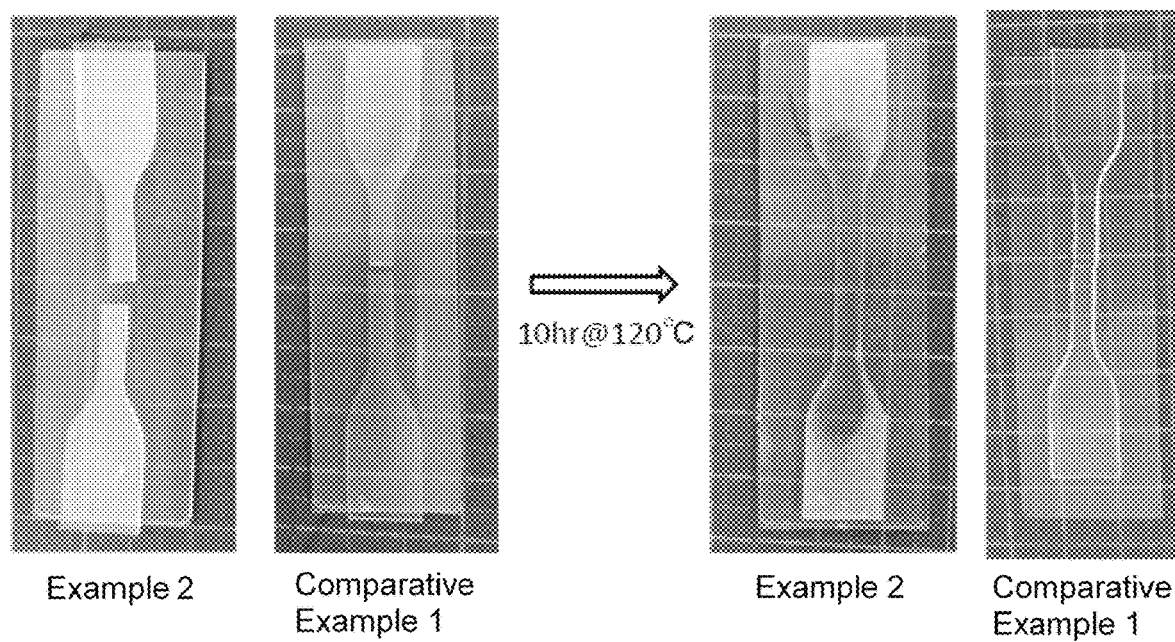

COMPOUND, COMPOSITION CONTAINING SAID COMPOUND, SELF-HEALING MATERIAL, SURFACE COATING AGENT, PAINT, ADHESIVE, MATERIAL FOR BATTERY AND CURED PRODUCT

TECHNICAL FIELD

The present invention relates to a novel compound having a specific structure, a composition including the compound, and a cured product obtained by curing the composition. The composition can be used in applications of a surface coating agent, a paint, an adhesive, and a self-healing material.

BACKGROUND ART

A polymer material shows high mechanical strength and high durability on the basis of a strong covalent bond. Meanwhile, the material is poor in re-processability and reusability, and hence the repairing of a scratch or rupture in the material, in particular, the self-healing thereof is difficult.

As a self-healable material that is excellent in durability and re-processability, and can be easily repaired, there has been known an approach based on an intermolecular interaction, such as a host-guest interaction (see, for example, Patent Documents 1 and 2), a self-healing material utilizing a dangling chain bonded to a polymer crosslinked structure (see, for example, Patent Document 3), or a technology (see, for example, Patent Documents 4 and 5) in which a microcapsule or the like having encapsulated therein a polymerizable monomer and a catalyst is blended into a matrix, such as a resin material, and at the time of damage to the matrix involving the breakage of the microcapsule or the like, a new monomer component is filled and polymerized to recover a function of the matrix. However, there have been such problems as described below. In each of the methods of Patent Documents 1 to 3, a complicated process is required for material production, and in each of the methods of Patent Documents 4 and 5, the number of times of self-healing is limited by, for example, the blending amount of the microcapsule. In addition, in recent years, to solve those problems, there has been known a self-healing material using reversible bond dissociation and recombination, which is obtained by applying an external stimulus to a material using a dynamic covalent bond (see, for example, Patent Document 6 and Non Patent Document 1). However, such self-healing material has a complicated molecular skeleton, and hence its synthesis process has been complicated and its productivity has been remarkably poor. Further, the self-healing power of the material has not been sufficient.

CITATION LIST

Patent Document

Patent Document 1: WO 2013/162019 A1
Patent Document 2: WO 2016/006413 A1
Patent Document 3: WO 2007/069765 A1
Patent Document 4: WO 2014/201290 A1
Patent Document 5: JP 2017-218519 A
Patent Document 6: JP 2017-202980 A

Non Patent Document

Non Patent Document 1: A. Takahashi, R. Goseki, K. Ito, H. Otsuka, ACS Macro Letters, 6, 1280 (2017).

SUMMARY OF INVENTION

Technical Problem

Accordingly, the present invention has been made in view of the above-mentioned problems and circumstances, and an object of the present invention is to provide a material having satisfactory productivity and excellent self-healing power.

Solution to Problem

The inventors of the present invention have made extensive investigations on, for example, causes for the problems with a view to solving the problems, and as a result, have found that a compound having a specific structure can solve the problems. Thus, the inventors have reached the present invention.

That is, the present invention is represented by the following items [1] to [10].

[1] A compound, which is represented by the following general formula (1):

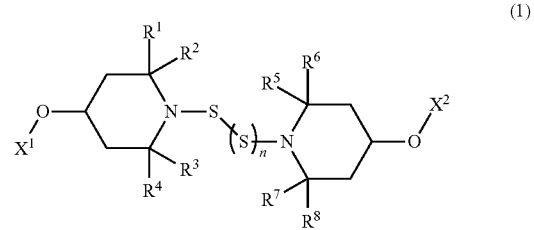

where $X^1$ and $X^2$ each independently represent an acrylic group or a methacrylic group, $R^1$ to $R^8$ each independently represent a hydrogen atom or a hydrocarbon group having 1 to 6 carbon atoms, and "n" represents an integer of from 1 to 10.

[2] The compound according to the above-mentioned item [1], wherein $R^1$ to $R^8$ in the general formula (1) each represent a methyl group.

[3] A composition, including the compound of the above-mentioned item [1] or [2].

[4] The composition according to the above-mentioned item [3], further including at least one kind of compound selected from the group consisting of a compound having an unsaturated hydrocarbon group, a compound having a thiol group, and a polymer compound.

[5] A self-healing material, which is obtained by using the composition of the above-mentioned item [3] or [4].

[6] A surface coating agent, including the composition of the above-mentioned item [3] or [4].

[7] A paint, including the composition of the above-mentioned item [3] or [4].

[8] An adhesive, including the composition of the above-mentioned item [3] or [4].

[9] A material for a battery, including the composition of the above-mentioned item [3] or [4].

[10] A cured product, which is obtained by curing the composition of the above-mentioned item [3] or [4].

Advantageous Effects of Invention

According to the present invention, the material having satisfactory productivity and excellent self-healing power can be provided.

BRIEF DESCRIPTION OF DRAWINGS

FIG. 1 shows photographs of samples in Example 2 and Comparative Example 1 after their cutting, and photographs of the samples subjected to heating treatment while their cut surfaces are brought into contact with each other after the cutting.

DESCRIPTION OF EMBODIMENTS

Now, detailed description is made of an embodiment of the present invention.

The symbols "n-", "i-", "s-", and "t-" as used herein mean normal, iso, secondary, and tertiary, respectively.

Herein, a compound having an acrylic group may be referred to as "acrylic compound" or "acrylate compound," and a compound having a methacrylic group may be referred to as "methacrylic compound" or "methacrylate compound."

A compound of the present invention is represented by the following general formula (1):

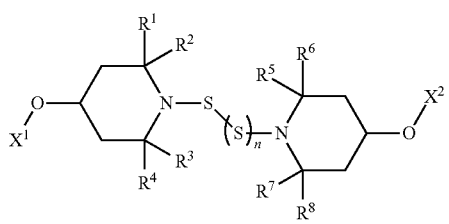

(1)

In the general formula (1), $X^1$ and $X^2$ each independently represent an acrylic group or a methacrylic group, $R^1$ to $R^8$ each independently represent a hydrogen atom or a hydrocarbon group having 1 to 6 carbon atoms, and "n" represents an integer of from 1 to 10.

The compound represented by the general formula (1) is characterized in that the compound has a polysulfide skeleton. A chemical bond between the sulfur atoms of the polysulfide skeleton easily undergoes cleavage and recombination through heating, light irradiation, or the like, and hence an investigation has been made on the utilization of the skeleton as the skeleton of a self-healing material as described in, for example, Patent Document 6 and Non Patent Document 1. However, each of the compounds described in Patent Document 6 and Non Patent Document 1 has a complicated molecular structure, and hence has involved, for example, a problem in that its productivity is low and its self-healing power is not sufficient. Meanwhile, the compound of the present invention enables simple synthesis of a compound having excellent self-healing power.

The excellent self-healing power refers to, for example, the following performance: the ability to repair even heavy damage; the number of times it can be repaired is large; or even when repaired from a damaged state, sufficient dynamic strength can be recovered. In particular, the compound of the present invention has the excellent self-healing power such as recovering the strength of the material before the damage.

Examples of the hydrocarbon group having 1 to 6 carbon atoms, which is represented by any one of $R^1$ to $R^8$ in the general formula (1), include a saturated aliphatic hydrocarbon group having 1 to 6 carbon atoms and an aromatic hydrocarbon group.

Specific examples thereof include: saturated aliphatic hydrocarbon groups, such as a methyl group, an ethyl group, a propyl group, an i-propyl group, a butyl group, a 2-butyl group, an i-butyl group, a t-butyl group, a pentyl group, a 2-pentyl group, a 3-pentyl group, an i-pentyl group, a hexyl group, a 2-hexyl group, a 3-hexyl group, a cyclopentyl group, and a cyclohexyl group; unsaturated aliphatic hydrocarbon groups, such as a vinyl group, an allyl group, a butenyl group, a pentenyl group, a hexenyl group, a cyclopentenyl group, and a cyclohexenyl group; and aromatic hydrocarbon groups, such as a phenyl group. The saturated aliphatic hydrocarbon group and the unsaturated aliphatic hydrocarbon group may each be of a linear structure, a branched structure, or a cyclic structure.

Each of $R^1$ to $R^8$ in the general formula (1) preferably represents a hydrogen atom, a methyl group, an ethyl group, a propyl group, a butyl group, a t-butyl group, or a phenyl group from the viewpoint of the expression of more excellent self-healing power, and more preferably represents a methyl group or an ethyl group, and most preferably represents a methyl group.

"n" in the general formula (1) preferably represents an integer of from 1 to 8 from the viewpoint of the expression of more excellent self-healing power, and more preferably represents an integer of from 1 to 5, and most preferably represents an integer of from 1 to 3.

Of the compounds each represented by the general formula (1), the following compounds No. 1 to No. 20 in each of which $X^1$ and $X^2$ each represent a methacrylic group, and "n" represents from 1 to 5 are preferred, and the following compounds No. 1 to No. 16 in each of which $X^1$ and $X^2$ each represent a methacrylic group, and "n" represents 1 are more preferred. Further, compounds obtained by replacing methacrylic groups in the compounds No. 1 to No. 20 with acrylic groups are also preferred.

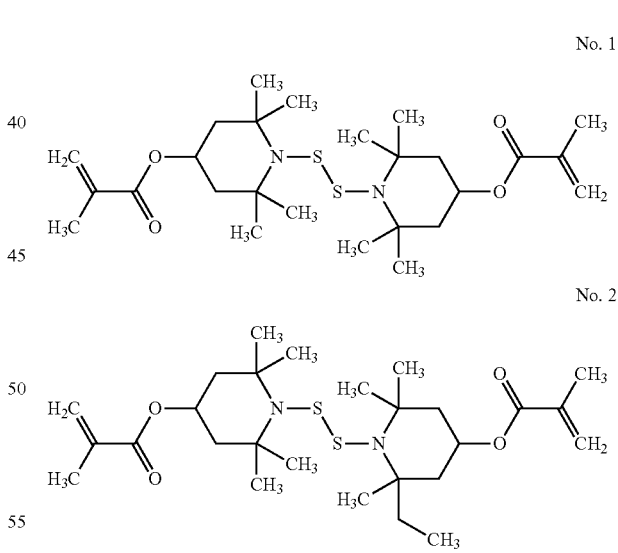

No. 1

No. 2

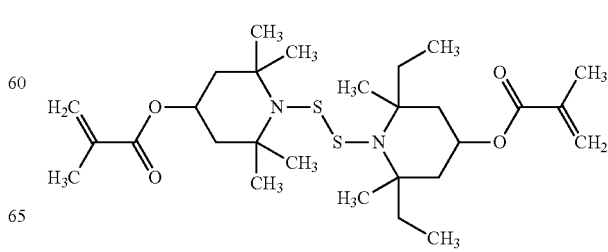

No. 3

-continued
No. 4
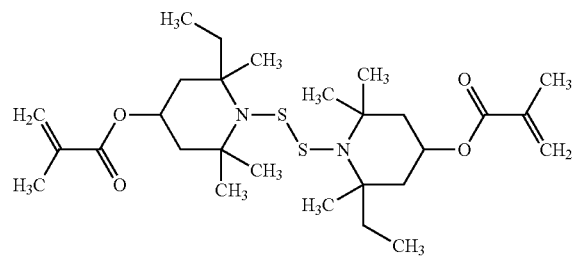
No. 5
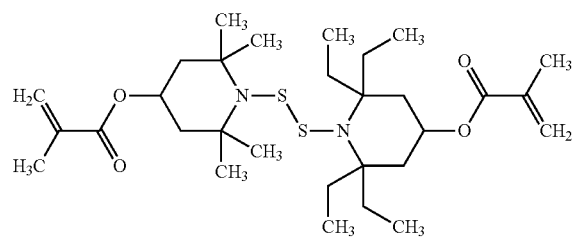
No. 6
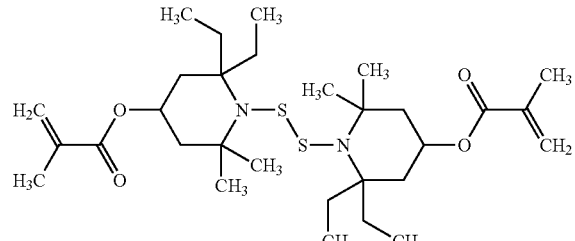
No. 7
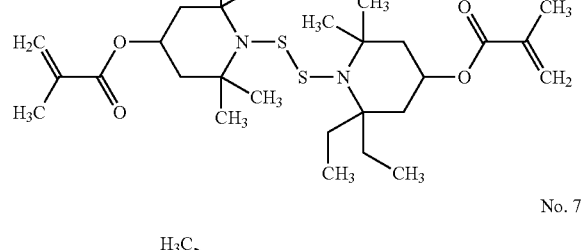
No. 8
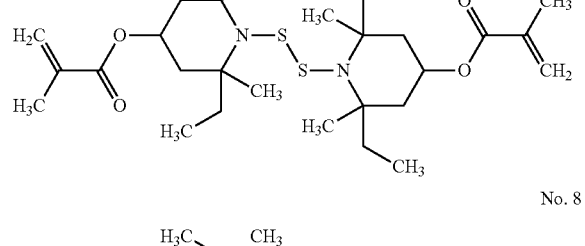
No. 9
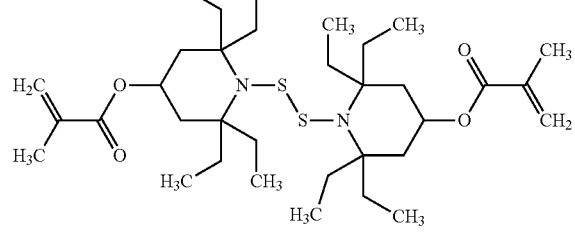
-continued
No. 10
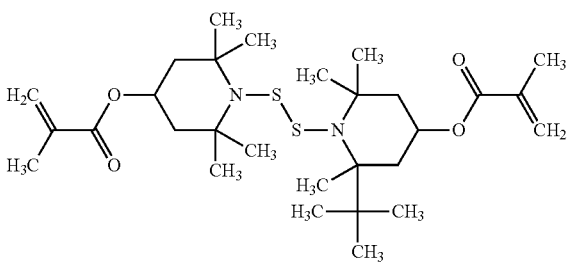
No. 11
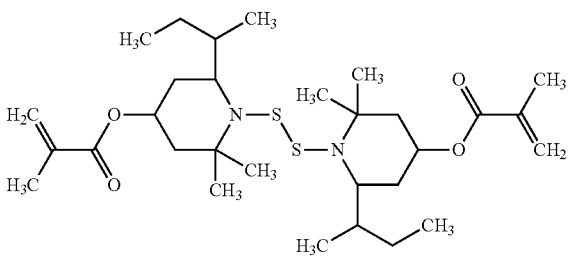
No. 12
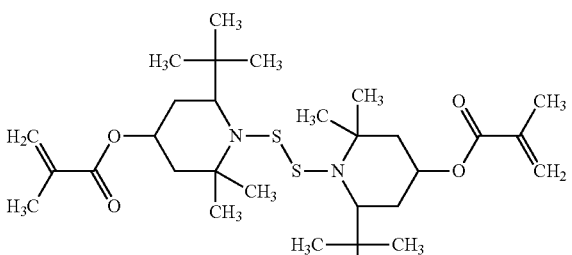
No. 13
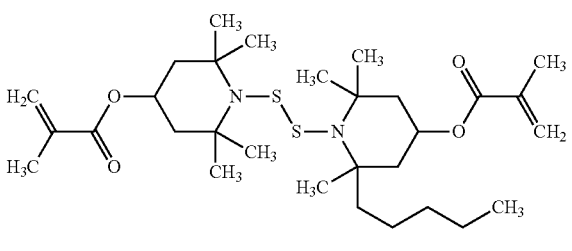
No. 14
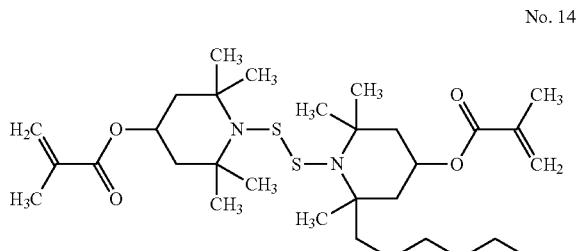

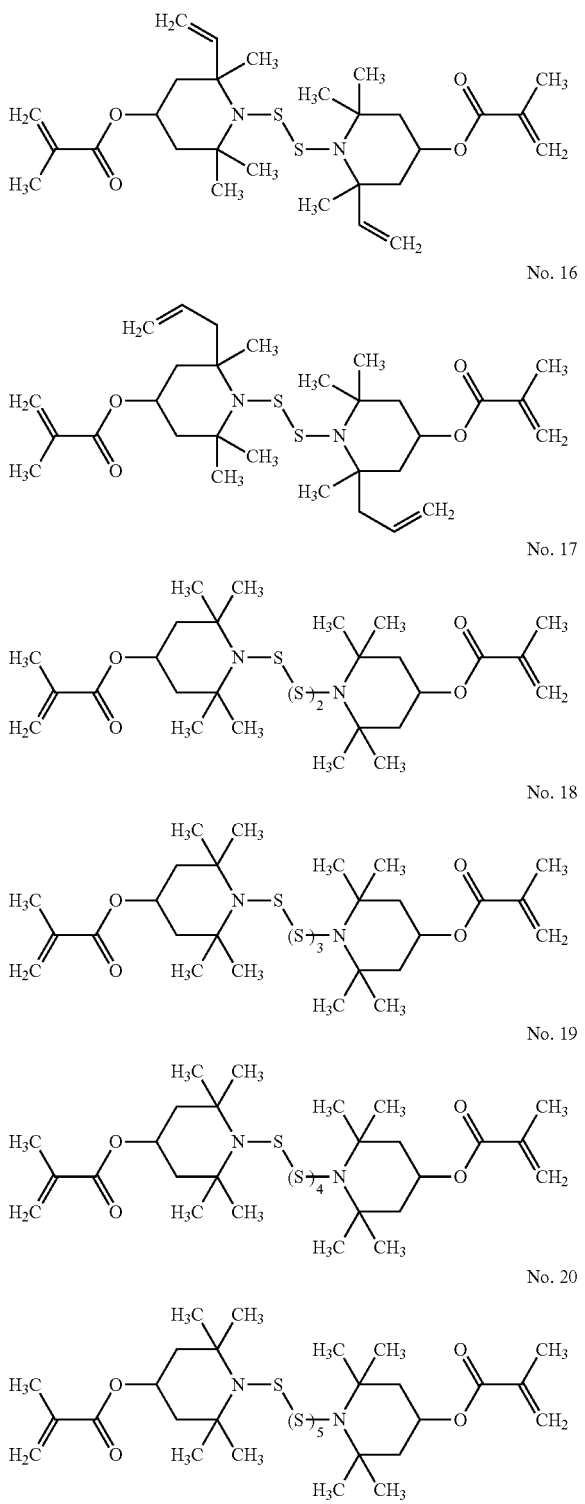

The compound represented by the general formula (1) can be produced by a simple method as compared to the related-art self-healing material. In the case of, for example, the compound No. 1, 2,2,6,6-tetramethyl-4-piperidyl methacrylate, sodium acetate, and dehydrated dimethylformamide are loaded into a reaction vessel, and disulfur dichloride is dropped from an isobaric dropping funnel while the temperature of the mixture is maintained at 0° C. under a nitrogen atmosphere. After the dropping, while the temperature is maintained at 0° C., the mixture is stirred for 10 minutes. After that, ice water is poured into the reaction solution, and the resultant precipitate is separated by filtration and recovered. The precipitate is dissolved in hexane and dried with sodium sulfate, followed by condensation under reduced pressure. After that, the condensate is recrystallized with methanol. Thus, the compound can be obtained. The other compounds can each be synthesized by using a piperidyl derivative having the corresponding substituent.

A composition of the present invention only needs to include the compound represented by the general formula (1), and a component to be used in combination with the compound represented by the general formula (1) is not particularly limited, but is, for example, a monomer compound, a polymer compound, a catalyst, a polymerization initiator, or an organic solvent.

Although the monomer compound is not particularly limited, a compound that can provide a polymer compound with itself through a polymerization reaction, and a compound that can be copolymerized with the compound represented by the general formula (1) are preferred, and a compound having an unsaturated hydrocarbon group and a compound having a thiol group are more preferred.

Examples of the compound having an unsaturated hydrocarbon group include a compound having a vinyl group, a compound having an allyl group, an acrylate compound, and a methacrylate compound.

Examples of the compound having a vinyl group or the compound having an allyl group that may be used in the composition of the present invention include: alkene compounds, such as ethylene, propene, 1-butene, 2-butene, i-butene, 1-pentene, 1-hexene, and 1-octene; cyano group-containing unsaturated hydrocarbon compounds, such as acrylonitrile, methacrylonitrile, α-chloroacrylonitrile, and α-cyanoethyl acrylonitrile; vinyl ether compounds, such as vinyl ethyl ether, vinyl butyl ether, vinyl phenyl ether, vinyl 2-chloroethyl ether, 3,4-dihydro-2H-pyran, 2,3-dihydrofuran, 1,4-dioxene, ethylene glycol monovinyl ether, diethylene glycol monovinyl ether, and isopropenyl methyl ether; vinyl ester compounds, such as vinyl acetate, vinyl butyrate, isopropenyl acetate, vinyl caprate, and vinyl benzoate; unsaturated alcohols, such as allyl alcohol and cinnamyl alcohol; conjugated diene compounds, such as 1,3-butadiene, isoprene, 1,3-pentadiene, 1,3-hexadiene, 1,3-cyclohexadiene, 1,3-cycloheptadiene, 1,3-cyclooctadiene, 2,5-dimethyl-2,4-hexadiene, and chloroprene; aromatic vinyl compounds, such as styrene, 2-methylstyrene, 3-methylstyrene, 4-methylstyrene, 2,4,6-trimethylstyrene, 4-butylstyrene, 4-phenylstyrene, 4-fluorostyrene, 2,3,4,5,6-pentafluorostyrene, 4-chlorostyrene, 4-bromostyrene, 4-iodostyrene, 4-hydroxystyrene, 4-aminostyrene, 4-carboxystyrene, 4-acetoxystyrene, 4-cyanomethylstyrene, 4-chloromethylstyrene, 4-methoxystyrene, 4-nitrostyrene, sodium 4-styrenesulfonate, 4-styrenesulfonyl chloride, 4-vinylphenylboronic acid, α-methylstyrene, trans-β-methylstyrene, 2-methyl-1-phenylpropene, 1-phenyl-1-cyclohexene, β-bromostyrene, sodium β-styrenesulfonate, 2-vinylpyridine, 4-vinylpyridine, 2-i-propenylnaphthalene, and 1-vinylimidazole; and allylbenzene and triallyl cyanurate.

Examples of the acrylate compound that may be used in the composition of the present invention include a monofunctional acrylate compound, a bifunctional acrylate compound, and a polyfunctional acrylate compound that is trifunctional or more.

Examples of the monofunctional acrylate compound include alkyl acrylates, such as methyl acrylate, ethyl acrylate, n-propyl acrylate, i-propyl acrylate, n-butyl acrylate, i-butyl acrylate, t-butyl acrylate, n-pentyl acrylate, i-pentyl acrylate, t-pentyl acrylate, neopentyl acrylate, hexyl acrylate, octyl acrylate, dodecyl acrylate, and stearyl acrylate, benzyl acrylate, an acrylate of an alkylphenol (e.g., butylphenol, octylphenol, nonylphenol, or dodecylphenol) ethylene oxide adduct, isobornyl acrylate, cyclohexyl acrylate, tricyclodecane monomethylol acrylate, 2-hydroxyethyl acrylate, 2-hydroxypropyl acrylate, 3-hydroxypropyl acrylate, 2-hydroxybutyl acrylate, 4-hydroxybutyl acrylate, hydroxypentyl acrylate, 2-hydroxy-3-phenoxypropyl acrylate, 2-hydroxy-3-butoxypropyl acrylate, 2-hydroxy-3-methoxypropyl acrylate, diethylene glycol monoacrylate, triethylene glycol monoacrylate, polyethylene glycol monoacrylate, dipropylene glycol monoacrylate, polypropylene glycol monoacrylate, glycerin monoacrylate, acryloxyethyl phthalate, 2-acryloyloxyethyl-2-hydroxyethyl phthalate, 2-acryloyloxypropyl phthalate, β-carboxyethyl acrylate, an acrylic acid dimer, ω-carboxy-polycaprolactone monoacrylate, dimethylaminoethyl acrylate, diethylaminoethyl acrylate, N-vinylpyrrolidone, N-vinylformamide, and acryloylmorpholine.

Examples of the bifunctional acrylate compound include ethylene glycol diacrylate, diethylene glycol diacrylate, triethylene glycol diacrylate, polyethylene glycol diacrylate, propylene glycol diacrylate, dipropylene glycol diacrylate, tripropylene glycol diacrylate, polypropylene glycol diacrylate, butylene glycol diacrylate, pentyl glycol diacrylate, neopentyl glycol diacrylate, hydroxypivalyl hydroxypivalate diacrylate, hydroxypivalyl hydroxypivalate dicaprolactonate diacrylate, 1,6-hexanediol diacrylate, 1,2-hexanediol diacrylate, 1,5-hexanediol diacrylate, 2,5-hexanediol diacrylate, 1,7-heptanediol diacrylate, 1,8-octanediol diacrylate, 1,2-octanediol diacrylate, 1,9-nonanediol diacrylate, 1,2-decanediol diacrylate, 1,10-decanediol diacrylate, 1,2-decanediol diacrylate, 1,12-dodecanediol diacrylate, 1,2-dodecanediol diacrylate, 1,14-tetradecanediol diacrylate, 1,2-tetradecanediol diacrylate, 1,16-hexadecanediol diacrylate, 1,2-hexadecanediol diacrylate, 2-methyl-2,4-pentanediol diacrylate, 3-methyl-1,5-pentanediol diacrylate, 2-methyl-2-propyl-1,3-propanediol diacrylate, 2,4-dimethyl-2,4-pentanediol diacrylate, 2,2-diethyl-1,3-propanediol diacrylate, 2,2,4-trimethyl-1,3-pentanediol diacrylate, dimethyloloctane diacrylate, 2-ethyl-1,3-hexanediol diacrylate, 2,5-dimethyl-2,5-hexanediol diacrylate, 2-methyl-1,8-octanediol diacrylate, 2-butyl-2-ethyl-1,3-propanediol diacrylate, 2,4-diethyl-1,5-pentanediol diacrylate, 1,2-hexanediol diacrylate, 1,5-hexanediol diacrylate, 2,5-hexanediol diacrylate, 1,7-heptanediol diacrylate, 1,8-octanediol diacrylate, 1,2-octanediol diacrylate, 1,9-nonanediol diacrylate, 1,2-decanediol diacrylate, 1,10-decanediol diacrylate, 1,2-decanediol diacrylate, 1,12-dodecanediol diacrylate, 1,2-dodecanediol diacrylate, 1,14-tetradecanediol diacrylate, 1,2-tetradecanediol diacrylate, 1,16-hexadecanediol diacrylate, 1,2-hexadecanediol diacrylate, 2-methyl-2,4-pentane diacrylate, 3-methyl-1,5-pentanediol diacrylate, 2-methyl-2-propyl-1,3-propanediol diacrylate, 2,4-dimethyl-2,4-pentanediol diacrylate, 2,2-diethyl-1,3-propanediol diacrylate, 2,2,4-trimethyl-1,3-pentanediol diacrylate, dimethyloloctane diacrylate, 2-ethyl-1,3-hexanediol diacrylate, 2,5-dimethyl-2,5-hexanediol diacrylate, 2-butyl-2-ethyl-1,3-propanediol diacrylate, 2,4-diethyl-1,5-pentanediol diacrylate, tricyclodecane dimethylol diacrylate, tricyclodecane dimethylol dicaprolactonate diacrylate, a bisphenol A tetraethylene oxide adduct diacrylate, a bisphenol F tetraethylene oxide adduct diacrylate, a bisphenol S tetraethylene oxide adduct diacrylate, a hydrogenated bisphenol A tetraethylene oxide adduct diacrylate, a hydrogenated bisphenol F tetraethylene oxide adduct diacrylate, hydrogenated bisphenol A diacrylate, hydrogenated bisphenol F diacrylate, a bisphenol A tetraethylene oxide adduct dicaprolactonate diacrylate, and a bisphenol F tetraethylene oxide adduct dicaprolactonate diacrylate.

Examples of the trifunctional acrylate compound include glycerin triacrylate, trimethylolpropane triacrylate, trimethylolpropane tricaprolactonate triacrylate, trimethylolethane triacrylate, trimethylolhexane triacrylate, trimethyloloctane triacrylate, and pentaerythritol triacrylate.

Examples of the acrylate compound that is tetrafunctional or more include pentaerythritol tetraacrylate, pentaerythritol tetracaprolactonate tetraacrylate, diglycerin tetraacrylate, ditrimethylolpropane tetraacrylate, ditrimethylolpropane tetracaprolactonate tetraacrylate, ditrimethylolethane tetraacrylate, ditrimethylolbutane tetraacrylate, ditrimethylolhexane tetraacrylate, ditrimethyloloctane tetraacrylate, dipentaerythritol pentaacrylate, dipentaerythritol hexaacrylate, tripentaerythritol hexaacrylate, tripentaerythritol heptaacrylate, tripentaerythritol octaacrylate, and a tripentaerythritol polyalkylene oxide heptaacrylate.

Examples thereof also include polyfunctional acrylates, such as urethane acrylate and polyester acrylate.

Those acrylate compounds may be used alone or in combination thereof.

The acrylate compound that may be used in the composition of the present invention is preferably any one of a monofunctional acrylate compound and a bifunctional acrylate compound from the viewpoint that a cured product thereof shows excellent self-healing power, and the compound is more preferably a monofunctional acrylate compound.

Examples of the methacrylate compound that may be used in the composition of the present invention include a monofunctional methacrylate compound, a bifunctional methacrylate compound, and a polyfunctional methacrylate compound that is trifunctional or more.

Examples of the monofunctional methacrylate compound include alkyl methacrylates, such as methyl methacrylate, ethyl methacrylate, n-propyl methacrylate, propyl methacrylate, n-butyl methacrylate, i-butyl methacrylate, t-butyl methacrylate, n-pentyl methacrylate, i-pentyl methacrylate, t-pentyl methacrylate, neopentyl methacrylate, hexyl methacrylate, octyl methacrylate, dodecyl methacrylate, and stearyl methacrylate, benzyl methacrylate, a methacrylate of an alkylphenol (e.g., butylphenol, octylphenol, nonylphenol, or dodecylphenol) ethylene oxide adduct, isobornyl methacrylate, cyclohexyl methacrylate, tricyclodecane monomethylol methacrylate, 2-hydroxyethyl methacrylate, 2-hydroxypropyl methacrylate, 3-hydroxypropyl methacrylate, 2-hydroxybutyl methacrylate, 4-hydroxybutyl methacrylate, hydroxypentyl methacrylate, 2-hydroxy-3-phenoxypropyl methacrylate, 2-hydroxy-3-butoxypropyl methacrylate, 2-hydroxy-3-methoxypropyl methacrylate, diethylene glycol monomethacrylate, triethylene glycol monomethacrylate, polyethylene glycol monomethacrylate, dipropylene glycol monomethacrylate, polypropylene glycol monomethacrylate, glycerin monomethacrylate, acryloxyethyl phthalate, 2-acryloyloxyethyl-2-hydroxyethyl phthalate, 2-acryloyloxypropyl phthalate, β-carboxyethyl methacrylate, an acrylic acid dimer, ω-carboxy-polycaprolactone monomethacrylate, dim ethyl aminoethyl methacrylate, diethylaminoethyl methacrylate, N-vinylpyrrolidone, N-vinylformamide, and acryloylmorpholine.

Examples of the bifunctional methacrylate compound include ethylene glycol dimethacrylate, diethylene glycol dimethacrylate, triethylene glycol dimethacrylate, polyethylene glycol dimethacrylate, propylene glycol dimethacrylate, dipropylene glycol dimethacrylate, tripropylene glycol dimethacrylate, polypropylene glycol dimethacrylate, butylene glycol dimethacrylate, pentyl glycol dimethacrylate, neopentyl glycol dimethacrylate, hydroxypivalyl hydroxypivalate dimethacrylate, hydroxypivalyl hydroxypivalate dicaprolactonate dimethacrylate, 1,6-hexanediol dimethacrylate, 1,2-hexanediol dimethacrylate, 1,5-hexanediol dimethacrylate, 2,5-hexanediol dimethacrylate, 1,7-heptanediol dimethacrylate, 1,8-octanediol dimethacrylate, 1,2-octanediol dimethacrylate, 1,9-nonanediol dimethacrylate, 1,2-decanediol dimethacrylate, 1,10-decanediol dimethacrylate, 1,2-decanediol dimethacrylate, 1,12-dodecanediol dimethacrylate, 1,2-dodecanediol dimethacrylate, 1,14-tetradecanediol dimethacrylate, 1,2-tetradecanediol dimethacrylate, 1,16-hexadecanediol dimethacrylate, 1,2-hexadecanediol dimethacrylate, 2-methyl-2,4-pentanediol dimethacrylate, 3-methyl-1,5-pentanediol dimethacrylate, 2-methyl-2-propyl-1,3-propanediol dimethacrylate, 2,4-dimethyl-2,4-pentanediol dimethacrylate, 2,2-diethyl-1,3-propanediol dimethacrylate, 2,2,4-trimethyl-1,3-pentanediol dimethacrylate, dimethyloloctane dimethacrylate, 2-ethyl-1,3-hexanediol dimethacrylate, 2,5-dimethyl-2,5-hexanediol dimethacrylate, 2-methyl-1,8-octanediol dimethacrylate, 2-butyl-2-ethyl-1,3-propanediol dimethacrylate, 2,4-diethyl-1,5-pentanediol dimethacrylate, 1,2-hexanediol dimethacrylate, 1,5-hexanediol dimethacrylate, 2,5-hexanediol dimethacrylate, 1,7-heptanediol dimethacrylate, 1,8-octanediol dimethacrylate, 1,2-octanediol dimethacrylate, 1,9-nonanediol dimethacrylate, 1,2-decanediol dimethacrylate, 1,10-decanediol dimethacrylate, 1,2-decanediol dimethacrylate, 1,12-dodecanediol dimethacrylate, 1,2-dodecanediol dimethacrylate, 1,14-tetradecanediol dimethacrylate, 1,2-tetradecanediol dimethacrylate, 1,16-hexadecanediol dimethacrylate, 1,2-hexadecanediol dimethacrylate, 2-methyl-2,4-pentane dimethacrylate, 3-methyl-1,5-pentanediol dimethacrylate, 2-methyl-2-propyl-1,3-propanediol dimethacrylate, 2,4-dimethyl-2,4-pentanediol dimethacrylate, 2,2-diethyl-1,3-propanediol dimethacrylate, 2,2,4-trimethyl-1,3-pentanediol dimethacrylate, dimethyloloctane dimethacrylate, 2-ethyl-1,3-hexanediol dimethacrylate, 2,5-dimethyl-2,5-hexanediol dimethacrylate, 2-butyl-2-ethyl-1,3-propanediol dimethacrylate, 2,4-diethyl-1,5-pentanediol dimethacrylate tricyclodecane dimethylol dimethacrylate, tricyclodecane dimethylol dicaprolactonate dimethacrylate, a bisphenol A tetraethylene oxide adduct dimethacrylate, a bisphenol F tetraethylene oxide adduct dimethacrylate, a bisphenol S tetraethylene oxide adduct dimethacrylate, a hydrogenated bisphenol A tetraethylene oxide adduct dimethacrylate, a hydrogenated bisphenol F tetraethylene oxide adduct dimethacrylate, hydrogenated bisphenol A dimethacrylate, hydrogenated bisphenol F dimethacrylate, a bisphenol A tetraethylene oxide adduct dicaprolactonate dimethacrylate, and a bisphenol F tetraethylene oxide adduct dicaprolactonate dimethacrylate.

Examples of the trifunctional methacrylate compound include glycerin trimethacrylate, trimethylolpropane trimethacrylate, trimethylolpropane tricaprolactonate trimethacrylate, trimethylolethane trimethacrylate, trimethylolhexane trimethacrylate, trimethyloloctane trimethacrylate, and pentaerythritol trimethacrylate.

Examples of the methacrylate compound that is tetrafunctional or more include pentaerythritol tetramethacrylate, pentaerythritol tetracaprolactonate tetramethacrylate, diglycerin tetramethacrylate, ditrimethylolpropane tetramethacrylate, ditrimethylolpropane tetracaprolactonate tetramethacrylate, ditrimethylolethane tetramethacrylate, ditrimethylolbutane tetramethacrylate, ditrimethylolhexane tetramethacrylate, ditrimethyloloctane tetramethacrylate, dipentaerythritol pentamethacrylate, dipentaerythritol hexamethacrylate, tripentaerythritol hexamethacrylate, tripentaerythritol heptamethacrylate, tripentaerythritol octamethacrylate, and a tripentaerythritol polyalkylene oxide heptamethacrylate.

Examples thereof also include polyfunctional methacrylates, such as urethane methacrylate and polyester methacrylate.

Those methacrylate compounds may be used alone or in combination thereof.

The methacrylate compound that may be used in the composition of the present invention is preferably any one of a monofunctional methacrylate compound and a bifunctional methacrylate compound from the viewpoint that a cured product thereof shows excellent self-healing power, and the compound is more preferably a monofunctional methacrylate compound.

Examples of the compound having a thiol group that may be used in the composition of the present invention include an aliphatic thiol compound, an aromatic thiol compound, an aliphatic polythiol compound, a mercaptocarboxylic acid ester compound, a mercaptocarboxylic acid, and a mercapto ether.

Of those compounds each having a thiol group, a bifunctional thiol compound is preferred from the viewpoint that a cured product thereof shows excellent self-healing power. Specific examples of the bifunctional thiol compound include alkyl vinyl ether adducts of 1,2-ethanedithiol, 1,2-propanedithiol, 1,3-propanedithiol, 1,3-butanedithiol, 2,3-butanedithiol, 1,5-pentanedithiol, 1,6-hexanedithiol, 1,8-octanedithiol, 1,9-nonanedithiol, 1,10-decanedithiol, 1,2-benzenedithiol, 1,3-benzenedithiol, 1,4-benzenedithiol, 3,6-dichloro-1,2-benzenedithiol, toluene-3,4-dithiol, 1,5-naphthalenedithiol, ethylene glycol bis(thioglycolate), ethylene glycol bis(3-mercaptopropionate), 1,4-butanediol bisthioglycolate, tetraethylene glycol bis(3-mercaptopropionate), trimethylolpropane tris(thioglycolate), trimethylolpropane tris(3-mercaptopropionate), trimethylolpropane tris(3-mercaptobutyrate), tris[(3-mercaptopropionyloxy)-ethyl] isocyanurate, pentaerythritol tetrakis(thioglycolate), pentaerythritol tetrakis(3-mercaptopropionate), dipentaerythritol hexakis(3-mercaptopropionate), 1,4-bis(3-mercaptobutyryloxy)butane, pentaerythritol tetrakis(3-mercaptobutyrate), pentaerythritol tetrakis(3-mercaptobutyrate), 1,3,5-tris(3-mercaptobutyloxy ethyl)-1,3,5-triazine-2,4,6(1H,3H,5H)-trione, dimercaptodiethyl sulfide, 1,8-dimercapto-3,6-dithiaoctane, 1,2-bis[(2-mercaptoethyl)thio]-3-mercaptopropane, tetrakis(7-mercapto-2,5-dithiaheptyl)methane, trithiocyanuric acid, 1,2-benzenedimethane, thiol, 4,4'-thiobisbenzene thiol, 2-di-n-butylamino-4,6-dimercapto-s-triazine, 2-di-n-butylamino-4,6-dimercapto-s-triazine, 2,5-dimercapto-1,3,4-thiadiazole, 1,8-dimercapto-3,6-dioxaoctane, 1,5-dimercapto-3-thiapentane, trimercaptopropionic acid tris(2-hydroxyethyl)isocyanurate, 1,4-dimethylmercaptobenzene, 2,4,6-trimercapto-s-triazine, 2-(N,N-dibutylamino)-4,6-dimercapto-s-triazine, bis(4-(2-mercaptopropoxy)phenyl)methane, 1,1-bis(4-(2-mercaptopropoxy)phenyl)ethane, 2,2-bis(4-(2-mercaptopropoxy)phenyl)propane, 2,2-bis(4-(2-mercaptopropoxy)phenyl)butane, 1,1-bis(4-(2-mercaptopropoxy)phenyl)isobutane, 2,2-bis(4-(2-mercaptopropoxy)-3-methylphenyl)propane, 2,2-bis(4-(2-mercaptopropoxy)-5-methylphenyl)

propane, bis(2-(2-mercaptopropoxy)-5-methylphenyl)methane, 2,2-bis(4-(2-mercaptopropoxy)-3-t-butylphenyl)propane, tris(4-(2-mercaptopropoxy)phenyl)methane, 1,1,1-tris(4-(2-mercaptopropoxy)phenyl)ethane, bis(4-(2-mercaptobutoxy)phenyl)methane, 2,2-bis(4-(2-mercaptobutoxy)phenyl)propane, tris(4-(2-mercaptobutoxy)phenyl)methane, and 1,3,5-triazine-2,4,6-trithiol. However, the bifunctional thiol compound is not limited thereto. For example, commercially available products may be used as those bifunctional thiol compounds.

Other monomer compounds to be used in combination with the compound represented by the general formula (1) may include an epoxy compound and a polyol compound. When the epoxy compound is blended into the composition, a curing agent and a polymerization initiator for curing the epoxy compound may be further blended into the composition. When the polyol compound is blended into the composition, an isocyanate compound for curing the polyol compound may be further blended into the composition.

Examples of the epoxy compound that may be used in the composition of the present invention include a compound having a glycidyl group, a compound having an alicyclic epoxy group, an epoxy compound having a phenol as a precursor, an epoxy compound having an amine as a precursor, and an epoxy compound having a carboxylic acid as a precursor. Examples thereof also include: bisphenol-type epoxy resins, such as a bisphenol A-type epoxy resin and a bisphenol F-type epoxy resin; biphenyl-type epoxy resins, such as a biphenyl-type epoxy resin and a tetramethyl biphenyl-type epoxy resin; a dicyclopentadiene-type epoxy resin; a naphthalene-type epoxy resin; an alicyclic epoxy resin obtained from, for example, cyclohexanedimethanol or hydrogenated bisphenol A; novolac-type epoxy resins, such as a phenol novolac-type epoxy resin, a cresol novolac-type epoxy resin, a bisphenol A novolac-type epoxy resin, an epoxidized product that is a condensate of a phenol and an aromatic aldehyde having a phenolic hydroxy group, and a biphenyl novolac-type epoxy resin; a triphenylmethane-type epoxy resin; a tetraphenylethane-type epoxy resin; a dicyclopentadiene-phenol addition reaction-type epoxy resin; and a phenol aralkyl-type epoxy resin. Substitutes obtained by substituting those materials with an alkyl group or a halogen atom may also be used. In addition, those materials may be turned into modified epoxy resins with a urethane compound or an isocyanate compound.

Examples of the curing agent and the polymerization initiator for curing the epoxy compound include an imidazole compound, an amine compound, an amide compound, an acid anhydride compound, a phenol compound, a thiol compound, a latent heat curing agent, and a cationic polymerization initiator.

Examples of the imidazole compound include 2-undecylimidazole and a compound described in JP 2015-017059 A.

Examples of the amine compound include: aliphatic amine compounds, such as ethylenediamine, diethylenetriamine, and hexamethylenediamine; aryl aliphatic amine compounds, such as N-methylaniline, m-xylenediamine, p-xylenediamine, diphenylamine, and hydroxyphenylglycine; and cyclic aliphatic amine compounds, such as 1,3-bisaminomethylcyclohexane, N-methylpiperazine, morpholine, piperidine, isophoronediamine, and 4,4-methylenebiscyclohexaneamine.

An example of the amide compound is dicyandiamide.

Examples of the acid anhydride compound include tetrahydrophthalic anhydride, hexahydrophthalic anhydride, methyltetrahydrophthalic anhydride, methylhexahydrophthalic anhydride, methyl nadic anhydride, hydrogenated methyl nadic anhydride, a trialkyltetrahydrophthalic anhydride, methylcyclohexenetetracarboxylic dianhydride, phthalic anhydride, trimellitic anhydride, pyromellitic anhydride, benzophenonetetracarboxylic dianhydride, ethylene glycol bisanhydrotrimellitate, glycerin bis(anhydrotrimellitate) monoacetate, dodecenylsuccinic anhydride, an aliphatic dibasic acid polyanhydride, chlorendic anhydride, methylbutenyltetrahydrophthalic anhydride, an alkylated tetrahydrophthalic anhydride, methyl himic anhydride, succinic anhydride substituted with an alkenyl group, and glutaric anhydride.

Examples of the phenol compound include phenol novolac and cresol novolac.

Although a conventionally known compound may be used as the above-mentioned thiol compound, a compound represented by the following general formula (2) is particularly preferred in terms of heat resistance.

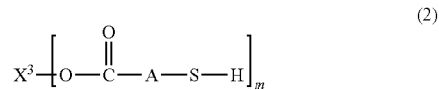

(2)

(In the formula, A represents an alkylene group having 1 to 10 carbon atoms, "m" represents an integer of from 1 to 6, and $X^3$ represents a saturated hydrocarbon group having 1 to 20 carbon atoms, the group having the same valence as "m".)

Examples of the above-mentioned latent heat curing agent include: a modified amine latent curing agent having at least one amino group having active hydrogen in a molecule obtained by causing a polyamine compound and an epoxy compound to react with each other; a latent curing agent containing a phenol-based resin; dicyandiamide; modified polyamine; hydrazides; 4,4'-diaminodiphenylsulfone; a boron trifluoride-amine complex salt; ureas; melamine; and latent curing agents described in WO 2012/020572 A1 and JP 2014-177525 A.

The cationic polymerization initiator only needs to be a compound that can release a substance configured to initiate cationic polymerization through light irradiation or heating, and a preferred example thereof is an onium salt.

The onium salt is, for example, a salt of a cation and an anion represented by $[M]^{r+}[G]^{r-}$.

Herein, the cation $[M]^{r+}$ is preferably an onium, and its structure may be represented by, for example, the formula $[(R^{13})_f Q]^{r+}$.

$R^{13}$ represents an organic group that has 1 to 60 carbon atoms and may contain any number of atoms except a carbon atom. "f" represents an integer of from 1 to 5. The "f" $R^{13}$s are independent of each other, and may be identical to or different from each other. In addition, at least one of "f" $R^{13}$s preferably represents an organic group having an aromatic ring. Q represents an atom or an atomic group selected from the group consisting of S, N, Se, Te, P, As, Sb, Bi, O, I, Br, Cl, F, and N=N. In addition, when the valence of the Q in the cation $[M]^{r+}$ is set to "q", a relationship of r=f−q needs to be valid (provided that N=N is treated as having a valence of 0).

In addition, specific examples of the anion $[G]^{r-}$ include: monovalent anions, such as: halide ions, such as a chloride ion, a bromide ion, an iodide ion, and a fluoride ion; inorganic anions, such as a perchlorate ion, a chlorate ion, a thiocyanate ion, a hexafluorophosphate ion, a hexafluoroantimonate ion, and a tetrafluoroborate ion; borate-based anions, such as tetrakis(pentafluorophenyl)borate, tetra(3,5-difluoro-4-methoxyphenyl)borate, tetrafluoroborate, tetraarylborate, and tetrakis(pentafluorophenyl)borate; organic sulfonic acid-based anions, such as a methanesulfonate ion, a dodecylsulfonate ion, a benzenesulfonate ion, a toluenesulfonate ion, a trifluoromethanesulfonate ion, a naphthalenesulfonate ion, a diphenylamine-4-sulfonate ion, a 2-amino-4-methyl-5-chlorobenzenesulfonate ion, a 2-amino-5-nitrobenzenesulfonate ion, a phthalocyaninesulfonate ion, a fluorosulfonate ion, a trinitrobenzenesulfonate anion, a camphorsulfonate ion, a nonafluorobutanesulfonate ion, a hexadecafluorooctanesulfonate ion, a sulfonate ion having a polymerizable substituent, and sulfonate ions described in, for example, JP H10-235999 A, JP H10-337959 A, JP H11-102088 A, JP 2000-108510 A, JP 2000-168223 A, JP 2001-209969 A, JP 2001-322354 A, JP 2006-248180 A, JP 2006-297907 A, JP H08-253705 A, JP 2004-503379 A, JP 2005-336150 A, and WO 2006/28006 A1; organic phosphoric acid-based anions, such as an octyl phosphate ion, a dodecyl phosphate ion, an octadecyl phosphate ion, a phenyl phosphate ion, a nonylphenyl phosphate ion, and a 2,2'-methylenebis(4,6-di-t-butylphenyl)phosphonate ion; and a bistrifluoromethylsulfonylimide ion, a bisperfluorobutanesulfonylimide ion, a perfluoro-4-ethylcyclohexanesulfonate ion, a tetrakis(pentafluorophenyl)borate ion, and a tris(fluoroalkylsulfonyl)carboanion; and divalent anions, such as a benzenedisulfonate ion and a naphthalenedisulfonate ion.

Of such onium salts, aromatic sulfonium salts, such as an aryl diazonium salt, a diaryl iodonium salt, and a triaryl sulfonium salt, may be preferably used in the composition of the present invention.

Commercially available salts may be used as the aromatic sulfonium salts. Examples thereof include WPAG-336, WPAG-367, WPAG-370, WPAG-469, and WPAG-638 (manufactured by Wako Pure Chemical Industries, Ltd.), CPI-100P, CPI-101A, CPI-200K, and CPI-210S (manufactured by San-Apro Ltd.), and ADEKA ARKLS SP-056, ADEKA ARKLS SP-066, ADEKA ARKLS SP-130, ADEKA ARKLS SP-140, ADEKA ARKLS SP-082, ADEKA ARKLS SP-103, ADEKA ARKLS SP-601, ADEKA ARKLS SP-606, ADEKA ARKLS SP-701, ADEKA ARKLS SP-150, and ADEKA ARKLS SP-170 (manufactured by ADEKA Corporation).

The polyol compound that may be used in the composition of the present invention refers to a compound having two or more hydroxy groups in a molecule thereof, and each of the hydroxy groups may be an alcoholic hydroxy group, or may be a phenolic hydroxy group. Specific examples thereof include ethylene glycol, diethylene glycol, 1,2-propanediol, 2-methyl-1,3-propanediol, 1,3-propanediol, 1,4-butanediol, 1,3-butanediol, 2,3-butanediol, 1,5-pentanediol, 2-methyl-1,5-pentanediol, 3-methyl-1,5-pentanediol, 2,3,5-trimethyl-1,5-pentanediol, 1,6-hexanediol, 2-ethyl-1,6-hexanediol, 2,2,4-trimethyl-1,6-hexanediol, 2,6-hexanediol, 1,8-octanediol, 1,4-cyclohexanedimethanol, 1,2-dimethylolcyclohexane, 1,3-dimethylolcyclohexane, 1,4-dimethylolcyclohexane, 1,12-dodecanediol, polybutadienediol, neopentyl glycol, tetramethylene glycol, propylene glycol, dipropylene glycol, glycerin, trimethylolpropane, 1,3-dihydroxyacetone, hexylene glycol, 1,2,6-hexanetriol, ditrimethylolpropane, mannitol, sorbitol, pentaerythritol, a polyester polyol obtained by condensation polymerization between a polyol and a polycarboxylic acid or a hydroxycarboxylic acid, a polyether polyol obtained by adding ethylene oxide or propylene oxide to an alcohol or a phenol, a polyester polyol obtained by ring-opening polymerization of a lactone or the like, a polycarbonate polyol having a carbonate skeleton in a molecule thereof, a phenoxy resin, a polybutadiene having a hydroxy group, and an acrylic polyol.

Examples of the isocyanate compound for curing the polyol compound include: monofunctional isocyanate compounds, such as n-butyl isocyanate, isopropyl isocyanate, phenyl isocyanate, and benzyl isocyanate; polyfunctional isocyanate compounds, such as hexamethylene diisocyanate, 2,4-tolylene diisocyanate, 2,6-tolylene diisocyanate, 1,5-naphthalene diisocyanate, diphenylmethane-4,4'-diisocyanate, isophorone diisocyanate, xylylene diisocyanate, p-phenylene diisocyanate, 1,3,6-hexamethylene triisocyanate, and bicycloheptane triisocyanate; and terminal isocyanate group-containing compounds each obtained by a reaction between a polyfunctional isocyanate compound and an active hydrogen compound, such as trimethylolpropane.

Examples of the polymer compound that may be used in the composition of the present invention may include polyester, polyamide, polylactone, polystyrene, a polyalkylene oxide, polysiloxane, polydimethylsiloxane, polycarbonate, polylactide, polyolefin, polyisobutylene, polyamide imide, polyimide, polyphenol, polyurea, polyurethane urea, polyglucoside, polybutadiene, an epoxy resin, polyacetylene, polyvinyl, nylon, polyethylene terephthalate, polybutylene terephthalate, polyvinylidene chloride, polyacrylonitrile, polyacrylate, polymethacrylate, and polyvinyl alcohol, and copolymer compounds thereof, derivative compounds thereof, an epoxy cured product, a urethane cured product, a silicone resin, and a rubber component.

Examples of the epoxy cured product include products obtained by curing the epoxy compounds listed in the foregoing with the curing agents and the polymerization initiators for curing the epoxy compounds listed in the foregoing.

Examples of the urethane cured product include products obtained by causing the polyol compounds listed in the foregoing and the isocyanate compounds listed in the foregoing to react with each other.

Examples of the rubber component include: natural rubber, polybutadiene, polyisoprene, polyisobutylene, neoprene, polysulfide rubber, thiokol rubber, acrylic rubber, urethane rubber, silicone rubber, epichlorohydrin rubber, a styrene-butadiene block copolymer (SBR), a hydrogenated styrene-butadiene block copolymer (SEB), a styrene-butadiene-styrene block copolymer (SBS), a hydrogenated styrene-butadiene-styrene block copolymer (SEBS), a styrene-isoprene block copolymer (SIR), a hydrogenated styrene-isoprene block copolymer (SEP), a styrene-isoprene-styrene block copolymer (SIS), a hydrogenated styrene-isoprene-styrene block copolymer (SEPS), a styrene-butadiene random copolymer, a hydrogenated styrene-butadiene random copolymer, a styrene-ethylene-propylene random copolymer, a styrene-ethylene-butylene random copolymer, an ethylene-propylene copolymer (EPR), an ethylene-(1-butene) copolymer, an ethylene-(1-hexene) copolymer, an ethylene-(1-octene) copolymer, and an ethylene-propylene-diene copolymer (EPDM); and core shell-type rubber components, such as butadiene-acrylonitrile-styrene-core shell rubber (ABS), methyl methacrylate-butadiene-styrene-core shell rubber (MBS), methyl methacrylate-butyl acrylate-styrene-core shell rubber (MAS), octyl acrylate-butadiene-styrene-core shell rubber (MABS), an alkyl acrylate-butadiene-acrylonitrile-styrene core shell rubber (AABS), butadiene-styrene-core shell rubber (SBR), and siloxane-containing core shell rubber, such as methyl methacrylate-butyl acrylate siloxane.

When the composition of the present invention includes at least one kind of compound selected from the group consisting of the compound having an unsaturated hydrocarbon group, the compound having a thiol group, and the polymer compound, the blending amount of the compound represented by the general formula (1) is preferably from 0.01 mass % to 97 mass %, more preferably from 0.05 mass % to 95 mass %, most preferably from 0.1 mass % to 90 mass % with respect to the composition from the viewpoints of the reactivity of the composition and the physical properties of a cured product after the reaction of the composition.

In addition, from the viewpoint that the cured product shows excellent self-healing power, the blending amount of the at least one kind of compound selected from the group consisting of the compound having an unsaturated hydrocarbon group, the compound having a thiol group, and the polymer compound is preferably from 3 mass % to 99.99 mass %, more preferably from 5 mass % to 99.9 mass %, most preferably from 10 mass % to 99.0 mass % with respect to the composition.

The catalyst and the polymerization initiator that may be used in the composition of the present invention only need to be used as follows: a known catalyst and a known polymerization initiator are appropriately selected, and are used in known usage amounts and by known usage methods in accordance with, for example, the kinds and composition ratios of the compound represented by the general formula (1) and the other compound, such as the compound having an unsaturated hydrocarbon group.

A catalyst selected from known catalysts, the catalyst accelerating a reaction between the compound represented by the general formula (1) and, for example, the other compound in the composition, may be appropriately used as the catalyst that may be used in the composition of the present invention. For example, a catalyst selected from a typical metal catalyst, a metal compound catalyst, and a transition metal catalyst may be appropriately used.

The polymerization initiator that may be used in the composition of the present invention is not particularly limited, but is, for example, a radical generator.

Examples of the radical generator that may be used in the composition of the present invention include a photoradical generator configured to generate a radical through irradiation with light, such as UV light, and a thermal radical generator configured to generate a radical when heated. As specific examples of the photoradical generator, there may be used, for example, acetophenone, p-anisil, benzil, benzoin, benzophenone, 2-benzoylbenzoic acid, 4,4'-bis(diethylamino)benzophenone, 4,4'-bis(dimethylamino)benzophenone, benzoin methyl ether, benzoin-i-propyl ether, benzoin-i-butyl ether, benzoin ethyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxol-5-yl)-4,6-bis(trichloromethyl)-1,3,5-triazine, 2-benzyl-2-(dimethylamino)-4'-morpholinobutyrophenone, 4,4'-dichlorobenzophenone, 2,2'-diethoxyacetophenone, 2,4-diethylthioxanthen-9-one, diphenyl(2,4,6-trimethylbenzoyl)phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(methylthio)-2-morpholinopropiophenone, 2-i-nitrosopropiophenone, 2-phenyl-2-(p-toluenesulfonyloxy)acetophenone, 2,2-dimethoxy-2-phenylacetophenone, and phenylbis(2,4,6-trimethylbenzoyl)phosphine oxide. Those photoradical generators may be used alone or in combination thereof.

Examples of the thermal radical generator that may be used in the composition of the present invention include a peroxide and an azo-based compound. Specific examples of the thermal radical generator include: azo compounds, such as 2,2'-azobisisobutyronitrile, 2,2'-azobis(2,4-dimethylvaleronitrile), 2,2'-azobis(4-methoxy-2,4-dimethylvaleronitrile), dimethyl-2,2'-azobis(2-methylpropionate), dimethyl 2,2-azobis(i-butyrate), diethyl-2,2'-azobis(2-methylpropionate), and dibutyl-2,2'-azobis(2-methylpropionate); organic peroxides, such as t-butyl-2-ethyl peroxyhexanoate, dilauroyl peroxide, 1,1,3,3-tetramethylbutyl peroxy-2-ethylhexanoate, 1,1-di(t-hexylperoxy)cyclohexanone, di-t-butyl peroxide, t-butyl cumyl peroxide, 1,1-di(t-hexylperoxy)-3,3,5-trimethylcyclohexane, t-amylperoxy-2-ethylhexanoate, di(2-t-butylperoxyisopropyl)benzene, di(t-butyl)peroxide, benzoyl peroxide 1,1'-di(2-t-butylperoxyisopropyl)benzene, benzoyl peroxide, 1,1'-di(t-butylperoxy)cyclohexane, di(3, 5,5-trimethylhexanoyl) peroxide, t-butyl peroxyneodecanoate, t-hexyl peroxyneodecanoate, and dicumyl peroxide; and hydrogen peroxide. When a peroxide is used as the radical generator, the peroxide may be combined with a reducing agent to serve as a redox-type polymerization initiator. Those thermal radical generators may be used alone or in combination thereof.

In addition, the thermal radical generator and the photoradical generator may be used in combination.

The lower limit value of the blending amount of the thermal radical generator or the photoradical generator in the composition of the present invention is preferably 0.001 mass % or more with respect to the composition from the viewpoints of the reactivity of the composition and the physical properties of the cured product after the reaction, and the lower limit value is more preferably 0.005 mass % or more, most preferably 0.01 mass % or more. In addition, the upper limit value of the blending amount of the thermal radical generator or the photoradical generator is preferably 30 mass % or less with respect to the composition from the viewpoint of the storage stability of the composition, and the upper limit value is more preferably 25 mass % or less, most preferably 20 mass % or less.

The composition of the present invention may include an organic solvent for uniformly mixing its materials, or for obtaining satisfactory moldability and satisfactory film formability of the composition.

Examples of the organic solvent that may be used in the composition of the present invention include an alcohol-based solvent, a ketone-based solvent, an amide-based solvent, an ether-based solvent, an ester-based solvent, an aliphatic hydrocarbon-based solvent, an aromatic solvent, and a halogen-containing solvent.

Examples of the alcohol-based solvent may include: monoalcohol-based solvents, such as methanol, ethanol, n-propanol, i-propanol, n-butanol, i-butanol, s-butanol, t-butanol, n-pentanol, i-pentanol, 2-methylbutanol, s-pentanol, t-pentanol, 3-methoxybutanol, n-hexanol, 2-methylpentanol, s-hexanol, 2-ethylbutanol, s-heptanol, heptanol-3, n-octanol, 2-ethylhexanol, s-octanol, n-nonyl alcohol, 2,6-dimethylheptanol-4, n-decanol, s-undecyl alcohol, trimethylnonyl alcohol, s-tetradecyl alcohol, s-heptadecyl alcohol, furfuryl alcohol, phenol, cyclohexanol, methylcyclohexanol, 3,3,5-trimethylcyclohexanol, benzyl alcohol, and diacetone alcohol; polyhydric alcohol-based solvents, such as ethylene glycol, 1,2-propylene glycol, 1,3-butylene glycol, pentanediol-2,4, 2-methylpentanediol-2,4, hexanediol-2,5, heptanediol-2,4, 2-ethylhexanediol-1,3, diethylene glycol, dipropylene glycol, triethylene glycol, and tripropylene glycol; and polyhydric alcohol partial ether-based solvents, such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, and dipropylene glycol monopropyl ether. Those alcohol-based solvents may be used alone or in combination thereof.

Examples of the ketone-based solvent may include acetone, methyl ethyl ketone, methyl-n-propyl ketone, methyl-n-butyl ketone, diethyl ketone, methyl-1-butyl ketone, methyl-n-pentyl ketone, ethyl-n-butyl ketone, methyl-n-hexyl ketone, di-i-butyl ketone, trimethylnonanone, cyclopentanone, cyclohexanone, cycloheptanone, cyclooctanone, 2-hexanone, methylcyclohexanone, 2,4-pentanedione, acetonylacetone, diacetone alcohol, acetophenone, and fenchone. Those ketone-based solvents may be used alone or in combination thereof.

Examples of the amide-based solvent may include N,N-dimethylimidazolidinone, N-methylformamide, N,N-dimethylformamide, N,N-diethylformamide, acetamide, N-methylacetamide, N,N-dimethylacetamide, N-methylpropionamide, and N-methylpyrrolidone. Those amide-based solvents may be used alone or in combination thereof.

Examples of the ether-based solvent may include ethyl ether, i-propyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol dimethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol dimethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, tripropylene glycol monomethyl ether, tetrahydrofuran, 2-methyltetrahydrofuran, diphenyl ether, and anisole. Those ether-based solvents may be used alone or in combination thereof.

Examples of the ester-based solvent may include diethyl carbonate, propylene carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, i-amyl propionate, diethyl oxalate, di-n-butyl oxalate, methyl lactate, ethyl lactate, n-butyl lactate, n-amyl lactate, diethyl malonate, dimethyl phthalate, and diethyl phthalate. Those ester-based solvents may be used alone or in combination thereof.

Examples of the aliphatic hydrocarbon-based solvent may include n-pentane, i-pentane, n-hexane, i-hexane, n-heptane, i-heptane, 2,2,4-trimethylpentane, n-octane, i-octane, cyclohexane, and methylcyclohexane. Those aliphatic hydrocarbon-based solvents may be used alone or in combination thereof.

Examples of the aromatic hydrocarbon-based solvent may include benzene, toluene, xylene, ethylbenzene, trimethylbenzene, methylethylbenzene, n-propylbenzene, i-propylbenzene, diethylbenzene, i-butylbenzene, triethylbenzene, di-i-propylbenzene, n-amylnaphthalene, trimethylbenzene, tetralin, and anisole. Those aromatic hydrocarbon-based solvents may be used alone or in combination thereof.

Examples of the halogen-containing solvent may include dichloromethane, chloroform, chlorofluorocarbon, chlorobenzene, and dichlorobenzene. Those halogen-containing solvents may be used alone or in combination thereof.

The above-mentioned organic solvents may be used alone or in combination thereof. The kind and blending amount of such organic solvent may be appropriately selected in accordance with, for example, the viscosity of a solution of the materials for the composition and a shape into which the composition is molded. The blending amount of the organic solvent is preferably from 1 part by mass to 999 parts by mass, more preferably from 5 parts by mass to 499 parts by mass, most preferably from 10 parts by mass to 399 parts by mass with respect to 100 parts by mass of the composition from the viewpoint that the composition is easy to handle.

In addition, the composition of the present invention may be blended with a known additive, such as a UV absorber, a light stabilizer, an adhesive aid, a polymerization inhibitor, a sensitizer, an antioxidant, a smoothness-imparting agent, an alignment-controlling agent, an infrared absorber, a thixotropic agent, an antistatic agent, a defoaming agent, a colorant, an emulsifying agent, a surfactant, a photopolymerization initiator, a thermal polymerization initiator, a curing agent, a conductivity-imparting agent, a hydrolysis suppressor, a cellulose nanofiber, or a filling agent, such as a filler, at a known content by a known usage method.

Although the applications of the composition of the present invention are not particularly limited, the composition may be suitably used as a self-healing material. The self-healing material refers to the following material: when, under the use environment of the material, the material receives scratching, impact, or the like to cause a scratch or breakage, the material can be repaired without any external stimulus, or by a specific operation, treatment, or external stimulus. Examples of the external stimulus include contact, light irradiation, heating, and pressurization, and each of these external stimuli may be applied alone, or two or more kinds of the external stimuli may be applied sequentially or simultaneously.

The composition of the present invention may be used as a surface coating agent, a paint, an adhesive, or a material for a battery. The surface coating agent is used for the purpose of protecting the surface of a substrate, imparting a design property or optical characteristics to the substrate, controlling the physical properties of the surface, or imparting contamination resistance, drug resistance, weatherability, or the like to the substrate. The composition of the present invention only needs to be applied to the surface of the substrate by a known method, and examples thereof include a die coater method, a comma coater method, a curtain coater method, a spray coater method, a gravure coater method, a flexographic coater method, a knife coater method, a doctor blade method, a reverse roll method, a brush coating method, a dipping method, an inkjet method, and a wire bar coater method. When the composition of the present invention is used as the surface coating agent, the following only needs to be performed: the composition before its curing is applied to the surface of the substrate, and is then cured by a method to be described later. When the composition of the present invention is used as the surface coating agent, the paint, the adhesive, or the material for a battery, the composition may be blended with a known additive to be used in a surface coating agent, a paint, an adhesive, a material for a battery, or the like.

A cured product of the present invention is obtained by curing the composition of the present invention under specific conditions, and a production method therefor is not particularly limited.

The cured product of the present invention can be produced under known conditions and by a known method, and the conditions and the method may be appropriately selected in accordance with, for example, the blending amount of the compound represented by the general formula (1), the kind and blending amount of the compound selected from the group consisting of the compound having an unsaturated hydrocarbon group, the compound having a thiol group, and the polymer compound, and the kind and blending amount of the radical generator.

Specifically, the production may be performed by, for example, irradiating the composition with UV light or the like, or heating the composition to a temperature equal to or more than room temperature after the application of the composition to the substrate or the molding of the composition. One of the light irradiation and the heating may be performed, or the light irradiation and the heating may be alternately performed, may be simultaneously performed, or may be performed while their conditions are changed with time.

For example, a mercury lamp, a xenon lamp, a carbon arc lamp, a metal halide lamp, sunlight, a laser light source, or a LED light source may be used as a method for the light irradiation, and a UV-LED (wavelength: from 350 nm to 450 nm) is preferred as a light source in terms of operability. However, the light source only needs to be appropriately selected in accordance with the photoradical generator. Although an integrated irradiation dose only needs to be appropriately selected in accordance with, for example, the thickness of an object, the irradiation is preferably performed so that the integrated irradiation dose may fall within the range of, for example, from 1 mJ/cm$^2$ to 100,000 mJ/cm$^2$. This is because when the integrated irradiation dose is small, the reaction of the composition does not sufficiently progress. This is also because meanwhile, when the integrated irradiation dose is excessively large, the object may be colored. After the light irradiation, for example, heating treatment may be performed at a temperature in the range of from 50° C. to 200° C. for from about 1 second to about 24 hours.

The heating temperature is preferably set to 200° C. or less, and is more preferably set to 140° C. or less. In addition, the heating temperature is preferably set to 40° C. or more, and is more preferably set to 50° C. or more. Although the heating time only needs to be appropriately selected in accordance with the heating temperature or the like, the heating time is preferably from 1 second to 20 hours, more preferably from 10 seconds to 10 hours.

Although the cured product can be typically produced under atmospheric pressure, the production may be performed while a pressure is applied on condition that the pressure is 1,000 atm or less. An appropriate environment only needs to be selected as an atmosphere at the time of the production of the cured product in accordance with the composition of the composition or the like, and the production may be performed under an air atmosphere, or may be performed under an inert gas atmosphere, such as a nitrogen gas or an argon gas.

The cured product of the present invention can be produced by molding and curing the composition without using any organic solvent, or can be produced by molding and curing the composition after the adjustment of, for example, the viscosity of the composition with the organic solvent. In addition, the cured product thus produced may be dissolved in or swollen with a solvent, and molded or formed into a film. In addition, the cured product can be produced under the state of being emulsified or dispersed in water by emulsion polymerization or suspension polymerization in an aqueous system.

In the cured product of the present invention, the compound represented by the general formula (1), and at least one kind of compound selected from the group consisting of the compound having an unsaturated hydrocarbon group and the compound having a thiol group only need to be cured by a polymerization reaction therebetween. In addition, the mode of the polymerization reaction may be homopolymerization, or may be copolymerization. The hardness, strength, and the like of the cured product are not particularly limited.

With regard to the other applications of the composition and cured product of the present invention, the composition and the cured product may be suitably used in, for example, applications where satisfactory rupture resistance and satisfactory fatigue resistance are generally required, such as a sealing material, a heat-insulating material, a soundproof material, a coating agent, a sanitary material, a hose clip, a pipe for transporting a fluid, a flexible hose, a hotmelt adhesive, an additive for an adhesive, an optical material, an electrical apparatus, a battery material, a vehicle, a ship, an aircraft, a material for a building, housing, and architecture, a material of construction, clothing, a curtain, a sheet, a container, a pair of glasses, a bag case, and sporting goods.

More specific applications thereof include: an optical film; an optical sheet; an optical filter; a high-brightness prism sheet; an optical collector; an antireflection material, such as an antiglare film; a lighting apparatus; a transparent daylighting material; a protective film; a surface material for a pen input apparatus; an electrical cable; a sheath; an electric wire-covering material; a member for electrical insulation; an electronic instrument housing; a machine part; a vibration fatigue-resistant member; a capacitor; a separator for a secondary battery; a binder for a secondary battery; a solid electrolyte; a fiber-reinforced material; a rust inhibitor; a corrosion inhibitor; a paint, such as a spraying pigment or a barrier material (against organic matter, a gas, or moisture); a building material, such as a building material for a pet, a floor, a wall, or a door; a water-shielding sheet; a waterproof sheet; an actuator; a cleaning pad; a bathtub; a basin; a tub; a bathing helping product; an automotive material; an artificial leather; a synthetic leather; an artificial skin; a stent for endovascular treatment; a dental repair composite material; a sleeve material; a laminated glass; transfer foil; a flame-retardant film; a shaft for a writing instrument; a cushioning material; a buffer; an agricultural film; a decorative film; a decorative sheet; a sheet for a plastic greenhouse; an insect net; furniture; clothing; a bag; a pair of shoes; a pair of goggles; a ski; a snowboard; a racket; a tent; a container; a chopping board; a cutting board; an antibacterial film; an antibacterial molded body; a barrier film; and a packing.

A surface coating agent of the present invention has an alleviating effect on a processing failure caused by coating, and hence when the surface coating agent is used as, for example, a hard coat material for in-mold molding, processability at the time of molding processing can be improved.

A paint of the present invention has such an effect that a flaw in an applied coating film self-heals, and hence when the paint is used as, for example, a paint for an automobile, a flaw in the coating of the automobile can be repaired merely by heating without any repainting.

An adhesive of the present invention has such an effect that after a cured product after bonding has been cut, the cut pieces spontaneously join with each other, and hence the adhesive can alleviate a bonding failure and can be prevented from peeling owing to its deterioration. In addition, by virtue of the effect, a stress-relaxing effect can be imparted to the adhesive, and the adhesive strength of the adhesive can be improved.

A material for a battery of the present invention has such an effect that after a self-healing material in its resin has been cut, the cut pieces spontaneously join with each other, and hence when the material for a battery is used as, for example, a binder for a lithium ion secondary battery, the deterioration of battery performance due to the swelling and decomposition of an electrode at the time of repeated use of the battery can be prevented.

EXAMPLES

The present invention is specifically described below by way of Examples. However, the present invention is not limited thereto. In Examples, the expression "part(s)" or "%" is used, and represents "part(s) by mass" or "mass %" unless otherwise stated.

Example 1

Production of Compound No. 1

In a 1-liter four-necked flask made of glass, ADEKA STAB LA-87 (100 g, 443 mmol, manufactured by ADEKA CORPORATION) was dissolved in dimethylformamide (364 mL, dehydrated grade, manufactured by Tokyo Chemical Industry Co., Ltd.), and then sodium acetate (39.7 g, 484 mmol, manufactured by Tokyo Chemical Industry Co., Ltd.) was added to the solution, followed by stirring in an ice bath. The temperature of the liquid was cooled to 10° C. or less, and then disulfur dichloride (23.4 g, 173 mmol, manufactured by Tokyo Chemical Industry Co., Ltd.) was dropped into the liquid over 30 minutes so that the temperature of the liquid did not become 10° C. or more. After the dropping, under a state in which the flask was immersed in the ice bath, the mixture was stirred for 30 minutes to be subjected to a reaction. After that, the reaction liquid was loaded into water (500 mL) cooled in an ice bath, and the precipitated white solid was filtered out and recovered. The white solid was recrystallized with methanol twice, and was dried under reduced pressure to provide bis(4-(methacryloyloxy)-2,2,6,6-tetramethylpiperidin-1-yl)disulfide (BiTEMPS-MAc) represented below (16.9 g, yield: 19%).

The $^1$H-NMR of the resultant compound is as described below. $^1$H NMR) (600 MHz, in CDCl$_3$): δ/ppm, 6.07 (s, 2H), 5.54 (s, 2H), 5.14 (tt, 2H), 1.98 (dd, J=4.0 Hz, 12.4 Hz, 4H), 1.91 (s, 6H), 1.56 (t, J=4.0, 12.4 Hz, 4H), 1.45 (s, 12H), 1.24 (s, 12H)

As a result of the measurement of the high-resolution mass spectrum of the resultant compound, a signal having an M of 512.274 was obtained. In addition, as a result of the measurement of the low-resolution mass spectrum thereof, a signal having an M of 512,256 was obtained.

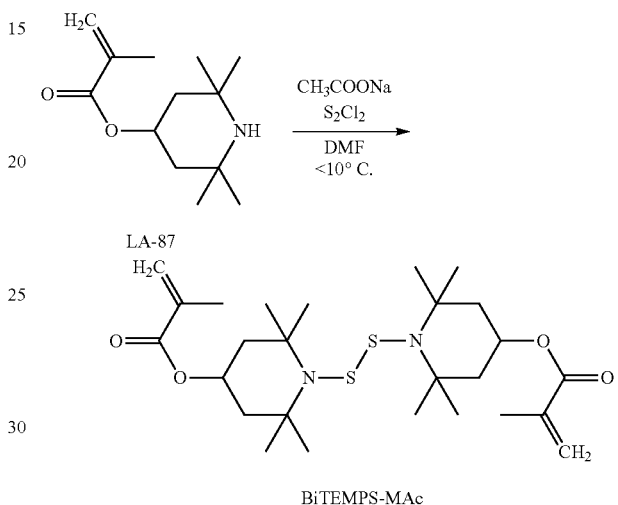

Example 2

10 Parts by mass of BiTEMPS-MAc obtained in Example 1, 90 parts by mass of 2-hydroxyethyl acrylate (LIGHT ESTER HOA(N), manufactured by Kyoeisha Chemical Co., Ltd.), and 1.0 part by mass of 2,2-dimethoxy-2-phenylacetophenone (manufactured by IGM Resins B.V.) were loaded into a flask, and were mixed while being stirred at 80° C. for 5 minutes. Thus, a composition was prepared. The composition was cast into a mold obtained by punching a silicone sheet having a thickness of 5 mm with a tensile test dumbbell cutter No. 6 (dumbbell No. 6 of JIS K 6251), and was cooled to room temperature. After that, in the air, the composition was irradiated with light from a high-pressure mercury lamp having an illuminance of 5 mW/cm$^2$ through a release PET film for 600 seconds to be cured. After having been left to stand for 5 minutes to be cooled, the cured product was removed from the mold to provide a dumbbell sample of Example 2. The center of the resultant dumbbell sample of Example 2 was cut with a cutter. After that, the cut surfaces were joined to each other, and the resultant was vertically sandwiched between glass plates. The laminate was vertically pinched with a clip to be fixed, and was left to stand in an oven at 120° C. for 10 hours. After the standing, the overlapping portions of the removed sample were integrated with each other to provide a uniform dumbbell.

Comparative Example 1

A dumbbell sample of Comparative Example 1 was produced in the same manner as in Example 2 except that 2,2-bis(4-(methacryloxydiethoxy)phenyl)propane (BPE-200, manufactured by SHIN-NAKAMURA CHEMICAL Co., Ltd.) was used instead of BiTEMPS-MAc. The resultant dumbbell sample of Comparative Example 1 was cut in the same manner as in the dumbbell sample of Example 2, and was sandwiched between glass plates. The laminate was pinched with a clip, and was left to stand in an oven at 120° C. for 10 hours. After the standing, the removed sample did not repair itself at all because its cut surfaces were not joined to each other.

In a tensile test, the sample of Example 2 that had repaired itself after the cutting showed a rupture strength corresponding to 97% of that of the sample subjected to the same thermal history (left to stand in an oven at 120° C. for 12 hours) without being cut, and hence the sample was found to have an excellent self-healing property.

Example 3

10 Parts by mass of BiTEMPS-MAc obtained in Example 1 and 90 parts by mass (in terms of solid content) of a styrene-butadiene rubber aqueous emulsion (BM-400B manufactured by Zeon Corporation) were loaded into a screw tube, and were mixed while being stirred with a pencil mixer for 5 minutes. Thus, a composition was prepared. The composition was cast into a mold obtained by punching a silicone sheet having a thickness of 1 mm with a tensile test dumbbell cutter No. 6 (dumbbell No. 6 of JIS K 6251). The composition was dried at 50° C. for 3 hours, and was further dried at 130° C. for 1 hour. The resin molded product was removed from the mold to provide a dumbbell sample of Example 3. The center of the resultant dumbbell sample of Example 3 was cut with a cutter. After that, the cut surfaces were joined to each other, and the resultant was vertically sandwiched between glass plates. The laminate was vertically pinched with a clip to be fixed, and was left to stand in an oven at 30° C. for 1 week. After the standing, the overlapping portions of the removed sample were integrated with each other to provide a uniform dumbbell.

Comparative Example 2

A dumbbell sample of Comparative Example 2 was produced in the same manner as in Example 3 except that 2,2-bis(4-(methacryloxydiethoxy)phenyl)propane (BPE-200, manufactured by SHIN-NAKAMURA CHEMICAL Co., Ltd.) was used instead of BiTEMPS-MAc. The resultant dumbbell sample of Comparative Example 2 was cut in the same manner as in the dumbbell sample of Example 3, and was sandwiched between glass plates. The laminate was pinched with a clip, and was left to stand in an oven at 30° C. for 1 week. After the standing, the removed sample did not repair itself at all because its cut surfaces were not joined to each other.

In a tensile test, the sample of Example 3 that had repaired itself after the cutting showed a rupture strength corresponding to 50% of that of the sample that was not cut, and hence the sample was found to have a self-healing property.

Example 4

10 Parts by mass of BiTEMPS-MAc obtained in Example 1, 90 parts by mass of hexyl methacrylate, 5.0 parts by mass of 2,2-dimethoxy-2-phenylacetophenone (manufactured by IGM Resins B.V.), and 1.0 part by mass of 2,2'-azobis(2,4-dimethylvaleronitrile) were loaded into a flask, and were mixed to prepare a composition. The composition was applied onto a glass plate, and a cover film was placed on the composition, followed by irradiation with light from a high-pressure mercury lamp having an illuminance of 3 mW/cm$^2$ for 660 seconds to cure the composition. Next, the composition was heated in an oven at 50° C. for 12 hours to be completely cured. Thus, a coating film sample of Example 4 was obtained. The resultant coating film sample of Example 4 was scratched with a 4B pencil, and was heated in an oven at 120° C. or 90° C., followed by the observation of the change of the scratch with time. In the coating film sample of Example 4, the manner in which the scratch repaired in 3 hours at 120° C. was able to be observed. In addition, in the coating film sample of Example 4, the manner in which the scratch repaired in 24 hours at 90° C. was able to be observed.

Comparative Example 3

A coating film sample of Comparative Example 3 was produced in the same manner as in Example 4 except that 2,2-bis(4-(methacryloxydiethoxy)phenyl)propane (BPE-200, manufactured by SHIN-NAKAMURA CHEMICAL Co., Ltd.) was used instead of BiTEMPS-MAc. The resultant coating film sample of Comparative Example 3 was scratched with a 4B pencil in the same manner as in the coating film sample of Example 4, and was heated in an oven at 120° C. or 90° C., followed by the observation of the change of the scratch with time. However, at each of the temperatures of 120° C. and 90° C., the scratch did not repair at all even after the lapse of 24 hours.

As can be seen from the foregoing results, according to the present invention, the material having excellent self-healing power was able to be obtained by a simple method including a small number of steps.

The invention claimed is:
1. A compound, which is represented by the following general formula (1):

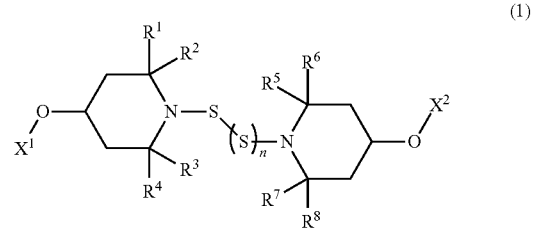

where $X^1$ and $X^2$ each independently represent an acrylic group or a methacrylic group, $R^1$ to $R^8$ each independently represent a hydrogen atom or a hydrocarbon group having 1 to 6 carbon atoms, and "n" represents an integer of from 1 to 10.

2. The compound according to claim 1, wherein $R^1$ to $R^8$ in the general formula (1) each represent a methyl group.

3. A composition, comprising the compound of claim 1.

4. The composition according to claim 3, further comprising at least one kind of compound selected from the group consisting of a compound having an unsaturated hydrocarbon group, a compound having a thiol group, and a polymer compound.

5. A self-healing material, which is obtained by using the composition of claim 3.

6. A surface coating agent, comprising the composition of claim 3.

7. A paint, comprising the composition of claim 3.

8. An adhesive, comprising the composition of claim 3.

9. A material for a battery, comprising the composition of claim 3.

10. A cured product, which is obtained by curing the composition of claim 3.

\* \* \* \* \*